(12) United States Patent
Cornett

(10) Patent No.: US 9,532,836 B2
(45) Date of Patent: Jan. 3, 2017

(54) LAYERED STERILE WORKSPACE ASSEMBLY

(71) Applicant: Edgar Stuart Cornett, Beckley, WV (US)

(72) Inventor: Edgar Stuart Cornett, Beckley, WV (US)

(*) Notice: Subject to any disclaimer, the term of this patent is extended or adjusted under 35 U.S.C. 154(b) by 0 days.

(21) Appl. No.: 14/723,571

(22) Filed: May 28, 2015

(65) Prior Publication Data

US 2015/0342684 A1  Dec. 3, 2015

Related U.S. Application Data

(60) Provisional application No. 62/003,662, filed on May 28, 2014.

(51) Int. Cl.
*A61B 19/02* (2006.01)

(52) U.S. Cl.
CPC .......... *A61B 19/0271* (2013.01); *A61B 46/10* (2016.02); *A61B 50/33* (2016.02); *A61B 2050/0065* (2016.02); *A61B 2050/3007* (2016.02)

(58) Field of Classification Search
CPC . A61B 19/38; A61B 19/0271; A61B 19/2019; A61B 19/0201; A61B 19/0219; A61B 19/0277; A61B 2050/0065; A61B 2050/3007; A61B 46/10; A61B 50/33
USPC ............ 220/62.13, 4.26, 4.27; 206/503, 509
See application file for complete search history.

(56) References Cited

U.S. PATENT DOCUMENTS

| 1,942,287 A | 1/1934 | Heitz |
| 3,579,669 A | 5/1971 | Loewenstein |
| 3,761,973 A | 10/1973 | Leventhal |
| 3,783,089 A * | 1/1974 | Hurst ..................... B29C 53/60 220/359.3 |

(Continued)

OTHER PUBLICATIONS

Anesthesia Quality Institute—Anesthesia Incident Reporting System (AIRS), Learning From Others: A Case Report from the Anesthesia Incident Reporting System, Newsletter, May 2013, 42-33, vol. 77, No. 5, American Society of Anesthesiologists, US.

(Continued)

*Primary Examiner* — J. Gregory Pickett
*Assistant Examiner* — Elizabeth Volz
(74) *Attorney, Agent, or Firm* — Dinsmore & Shohl, LLP; Monika L'Orsa Jaensson, Esq.

(57) ABSTRACT

The present invention regards a sterile workspace with removable layers for use on medical surfaces such as anesthesia workstations, as well as other surfaces. The assembly of the present invention generally includes a plurality of sterile workspaces, layered to form the assembly. Each workspace has a foam layer and a barrier layer. In some configurations, the workspace also has a tray, and the foam layer is secured to the top surface of the tray. The tray may have a raised border about its perimeter. In some configurations the foam layer has a non-porous bottom surface. The assembly may have a support surface under the bottom-most workspace layer, with an elastomer or adhesive affixed thereto to prevent the assembly from moving during use. The barrier layer is affixed to either the foam layer, or the tray (if present), and is removed to expose a sterile workspace when in use.

13 Claims, 9 Drawing Sheets

(56) References Cited

U.S. PATENT DOCUMENTS

| | | | |
|---|---|---|---|
| 4,015,709 A * | 4/1977 | Millet | A61M 5/002 |
| | | | 206/366 |
| 4,034,079 A | 7/1977 | Schoonman | |
| 4,107,811 A | 8/1978 | Imsande | |
| 4,167,230 A * | 9/1979 | Barratt | A61B 19/0288 |
| | | | 206/359 |
| 4,182,462 A | 1/1980 | Buff | |
| 5,084,927 A | 2/1992 | Parkevich | |
| 5,216,764 A | 6/1993 | Hall et al. | |
| 5,607,737 A | 3/1997 | Blackwell et al. | |
| 6,000,068 A | 12/1999 | Chavis | |
| 6,436,499 B1 | 8/2002 | Krampe et al. | |
| 6,458,442 B1 | 10/2002 | McKay | |
| 6,889,839 B1 | 5/2005 | Rosten et al. | |
| 7,040,484 B1 | 5/2006 | Homra et al. | |
| 7,600,274 B2 | 10/2009 | Washington | |
| 7,721,910 B2 | 5/2010 | Wallace | |
| 7,743,876 B2 | 6/2010 | Weidman | |
| 8,307,581 B2 | 11/2012 | Badgley et al. | |
| 2002/0064478 A1 * | 5/2002 | Davis | A61L 2/26 |
| | | | 422/26 |
| 2002/0112981 A1 | 8/2002 | Cooper et al. | |
| 2003/0064189 A1 | 4/2003 | Berg et al. | |
| 2005/0075023 A1 * | 4/2005 | Ayata | B32B 25/10 |
| | | | 442/103 |
| 2007/0215296 A1 | 9/2007 | Voutour | |
| 2007/0286878 A1 * | 12/2007 | Harruna | A01N 25/34 |
| | | | 424/405 |
| 2009/0158525 A1 | 6/2009 | Paszotta | |
| 2010/0032473 A1 * | 2/2010 | Grassia | B42F 21/02 |
| | | | 229/67.1 |
| 2010/0089408 A1 | 4/2010 | McCaughey et al. | |
| 2011/0127188 A1 * | 6/2011 | Thompson | B32B 27/18 |
| | | | 206/438 |
| 2011/0208103 A1 | 8/2011 | Leschinsky | |
| 2012/0043330 A1 * | 2/2012 | McLean | B32B 27/08 |
| | | | 220/359.2 |
| 2012/0292323 A1 * | 11/2012 | Young | B65D 43/0262 |
| | | | 220/276 |
| 2013/0142975 A1 | 6/2013 | Wallace | |

OTHER PUBLICATIONS

Kathleen Meehan Arias, MS, CIC, Contamination and Cross Contamination on Hospital Surfaces and Medical Equipment, Newsletter, 2010, 1-8, Initiatives in Safe Patient Care, US.

David Schwegman, M.D., Assistant Professor of Medicine, Prevention of Cross Transmission of Microorganisms is Essential to Preventing Outbreaks of Hospital Acquired Infections, Newsletter, 2008, Emory University, US.

International Search Report, Sep. 1, 2015, PCT/US2015/032865.

Written Opinion of the International Searching Authority, Sep. 1, 2015, PCT/US2015/032865.

* cited by examiner

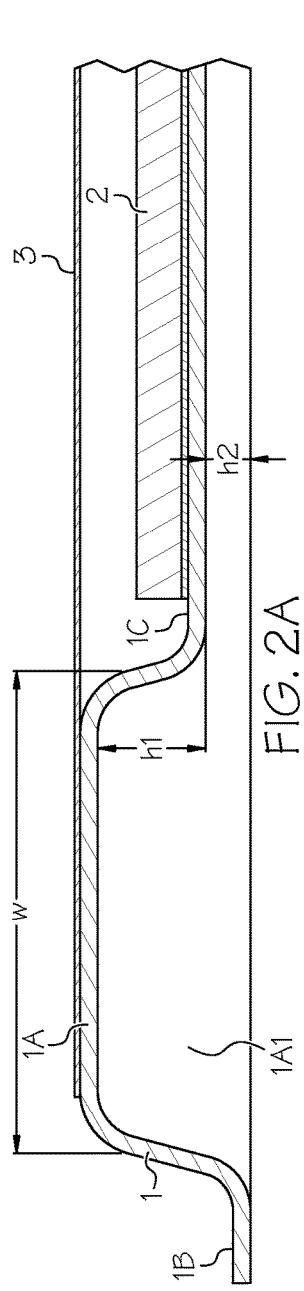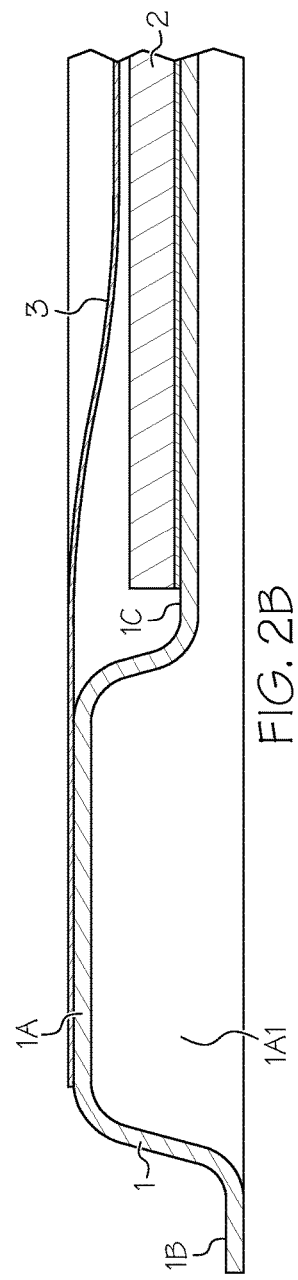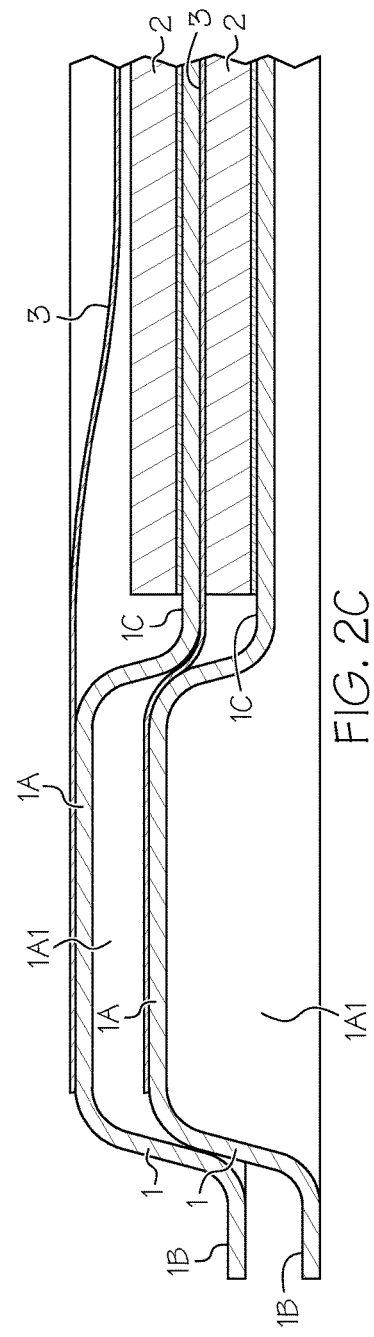

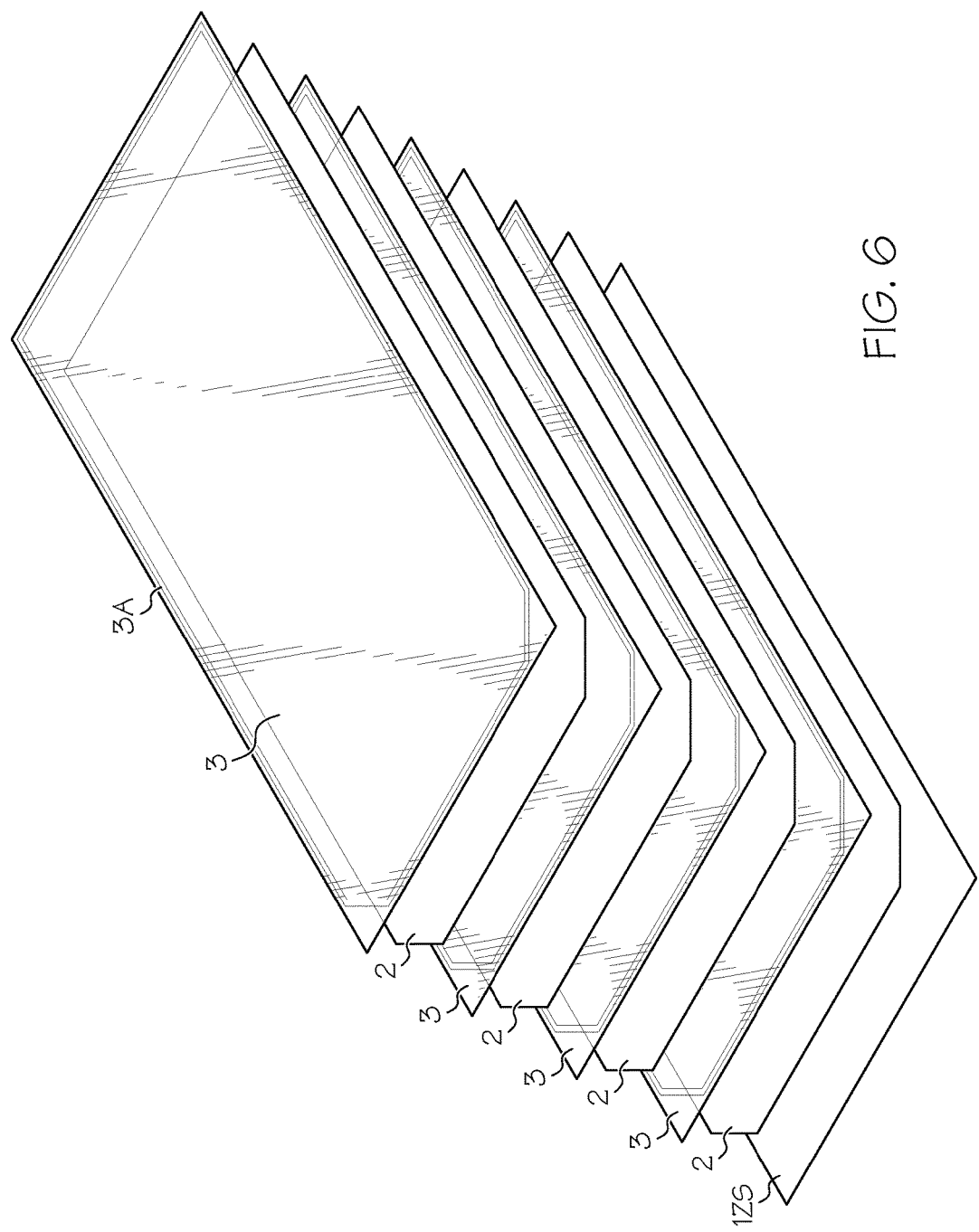

LAYERED STERILE WORKSPACE ASSEMBLY

BACKGROUND OF THE INVENTION

The present invention regards a sterile workspace with removable layers for use on medical surfaces such as anesthesia workstations, as well as other surfaces. Presently surfaces such as those provided on anesthesia machines must be sanitized between procedures to avoid patient cross contamination and potential nosocomial infections in operating rooms. The layered sterile assembly of the present invention provides a plurality of sanitized workspaces that remain independently sterilized until ready for use.

It is well established that the risk of infection from various drug-resistant organisms remains in operating and procedure rooms so long as work surfaces actively used in these environments are not properly cleaned and disinfected. While present methods of disinfecting work surfaces includes human application of disinfecting wipes, bleach and ultraviolet light, there is significant evidence that surface cleaning is not done as well as protocols require, and the risk of hospital acquired infections (HAI) transmitted from un-sanitized work surfaces remains high. The cost of HAI is significant, not only to human life but also to expenses resulting from increased length of patient stay and necessary healthcare. Financially, HAI has been estimated to contribute between $28-45 billion on the healthcare system. *A Case Report from the Anesthesia Incident Reporting System*, Anesthesia Quality Institute (May, 2013). Human cost from HAI has been estimated at over 99,000 deaths per year, or a 5% death rate. Schwegman, *Prevention of Cross Transmission of Microorganisms is Essential to Preventing Outbreaks of Hospital Acquired Infections*, Welch Allyn 2008.

While the necessity for sterility of medical devices has long been recognized and is consistently being optimized, both in device design and packaging, the sterility of work surfaces continues to be addressed through procedures and protocols susceptible to failure. Arias, *Contamination and Cross Contamination on Hospital Surfaces and Medical Equipment*, Initiatives in Safe Patient Care, Saxe Healthcare Communications, 2010. Therefore there is a need to consistently provide a sterile work surface for use in medical procedures, which overcomes human failures in comprehensively following established protocols to clean work surfaces, the use of which will result in a decrease in transmittal of HAI, benefitting the health of patients and mitigating a significant financial burden on the healthcare system.

GENERAL DESCRIPTION

The assembly of the present invention generally includes a plurality of sterile workspaces, layered to form the assembly. Each workspace has a foam layer. In some configurations the workspace also includes a tray, and the foam layer is secured to the top surface of the tray; the tray may have a raised border about its perimeter. In some configurations the foam layer has a non-porous bottom surface.

A barrier layer is affixed to either the foam layer, or the tray (if used), or both and is removed to expose the sterile workspace when desired. In some embodiments the bottom surface of each layer is removably adhered to the barrier layer of the next subsequent layer of the assembly. The assembly may have a support surface affixed to the bottom-most workspace layer, with an elastomer or adhesive provided on the bottom thereof to prevent the assembly from moving during use; alternatively, an elastomer or adhesive may be adhered to the bottom surface of the lowermost tray or foam layer of an assembly of the present invention.

By the present invention a plurality of sterile workspaces are provided in a single assembly, wherein while the topmost workspace may be used and contaminated, the sterility of the remaining workspaces below is retained. Removal of the top-most workspace exposes a subsequent workspace layer, which layer remains sterile until its barrier layer is removed at the beginning of the next procedure.

In use the assembly is positioned on a work surface, such as an accessory cart in an operating room. At the beginning of a procedure, the barrier layer of the top workspace layer is removed to expose the sterile foam layer, where tools and other equipment can be stored for use during the medical procedure. At the conclusion of the procedure, the entire topmost workspace layer is removed and discarded with other contaminated waste, exposing the next layer of the assembly. The barrier film of the newly exposed workspace layer remains on the layer until the beginning of the next procedure, thereby maintaining the sterility of the foam layer until the workspace is required for a procedure.

DESCRIPTION OF THE DRAWINGS

Embodiments of the present invention are shown in the accompanying figures, wherein:

FIGS. 2A and 2B are each a cutaway view of an embodiment of a sterile workspace layer of an assembly of the present invention.

FIG. 2C is a cutaway view of an embodiment of two sterile workspace layers of an assembly of the present invention.

FIG. 6 is a perspective view of another embodiment of multiple sterile workspace layers for an assembly of the present invention, with its components separated for illustration purposes only.

DETAILED DESCRIPTION

Figure 1A:
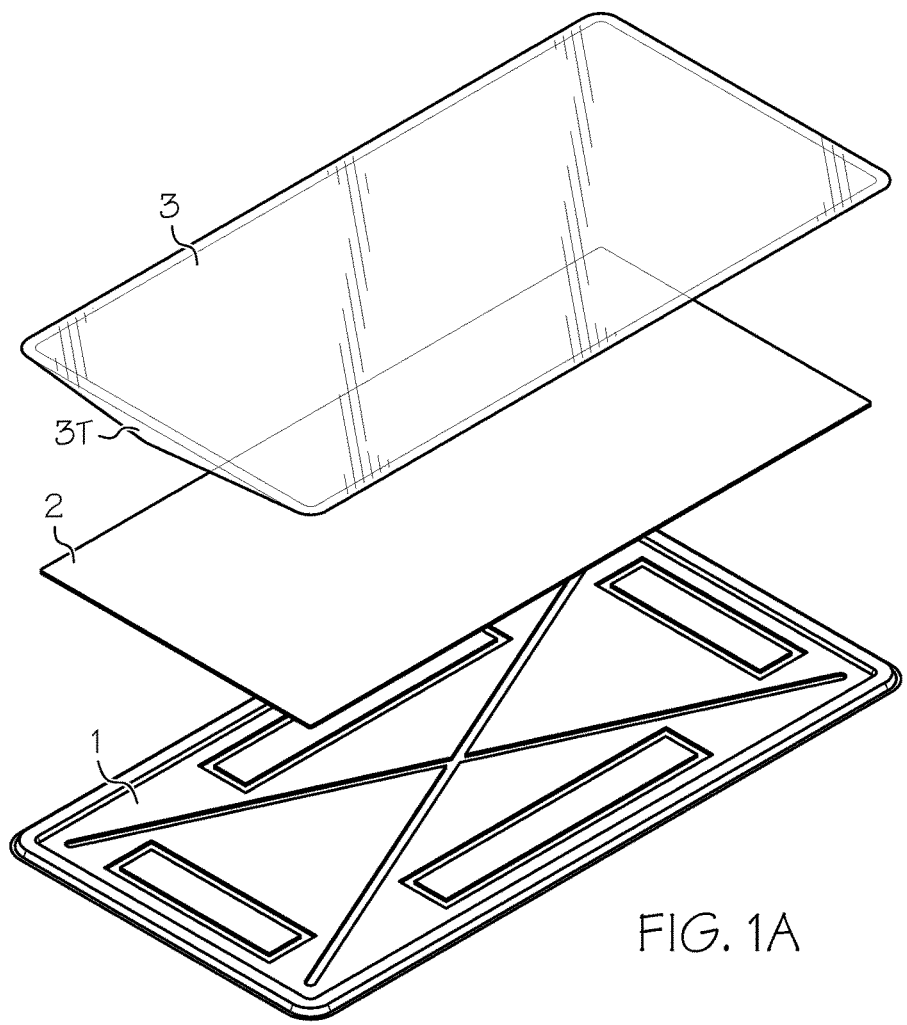
FIG. 1A is a perspective view of an embodiment of a sterile workspace layer of an assembly of the present invention, with its components separated.
Figure 1B:
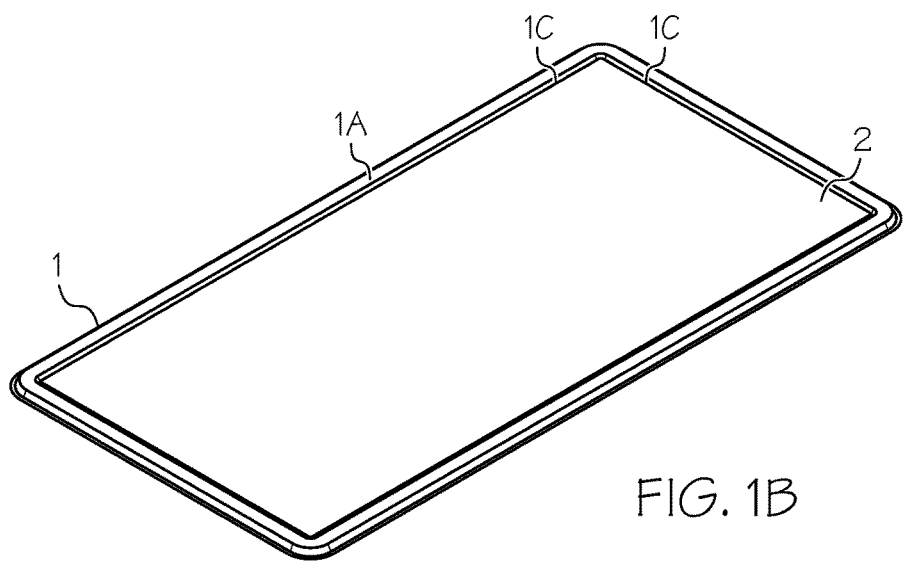
FIG. 1B is a perspective view of the tray and workspace of an embodiment of an assembly of the present invention.

The present invention provides a replaceable surface to assist with the prevention of cross contamination, in the form of an assembly of layered sterile workspaces. As shown in FIGS. 1A-5D, in some embodiments of the system of the present invention each layer of workspace includes a tray (1) and a workspace foam layer (2), with a barrier layer (3) removably affixed to the tray. As shown in FIG. 6, in other embodiments of the system of the present invention each layer of workspace includes a workspace foam layer (2), with a barrier layer (3) removably affixed thereto.

In the embodiment shown in FIGS. 1A-5D, the tray (1) of a workspace layer may be constructed of a medical grade, thermoformed thermoplastic; in some embodiments the tray is constructed from a medical grade polystyrene, in other embodiments it is constructed from medical grade high-density polyethylene (HDPE). The tray may also be constructed from PVC film, ionomer resin, polyimides, polyester, polypropylene, or polycarbonate, or any combination thereof. The tray is intended to have minimal thickness, for example about 0.01" to 0.025". The tray is sized and shaped to fit within the intended work surface, such as the work surface of accessory carts common to operating rooms (e.g., a tray sized 19.25"×10").

As shown in FIGS. 2A-C, the tray (1) may have a raised border (1A) about the perimeter and extending from the top surface of the tray, with a skirt (1B) extending from the outermost portion of the raised border and below the bottom surface of the tray. The height (h1) of the border (1A) creates a 'dam effect' on the top surface of the tray by preventing liquids collecting on the work surface from flowing off of the tray; the height of the border may be between about 0.08" and 0.15", or about 0.10" from the top surface of the tray; the height of the tray border above the foam top surface may be between about 0.04" and 0.08", or about 0.06". The skirt may extend below the bottom surface of the tray by a height (h2) about 0.025" to 0.075", or about 0.05", and may extend by about 0.1" to 0.25" from the perimeter of the raised border.

The raised border (1A) may have rounded edges, and may form a recess (1A1) sized to receive the raised border of the next tray in an assembly (as shown in FIG. 2C), thereby preventing lateral movement among the trays in the assembly. In some embodiments the raised border (1A) has a width w of between about 0.1" and 0.5", in some embodiments the width of the border before the rounded edges is about 0.375".

The tray may further have one or more support structures to support the integrity thereof during use. In one embodiment, shown in FIGS. 4A-4C, the tray is molded to include support structures in the form of a plurality of ribs (1R), which are hollow or filled, and which may cross on the bottom side of the tray, may be shaped in the form of one or more rectangles, or may be provided in another suitable configuration to support the structural integrity of the tray. The depressed area formed by any of these support structures may receive adhesive material or an elastomer, to removably affix the trays to one-another, or prevent slippage of the assembly on a work surface, as hereinafter described. Alternatively the adhesive or elastomer may be applied or affixed to the support structures, such as the ribs (1R).

Figure 3A:
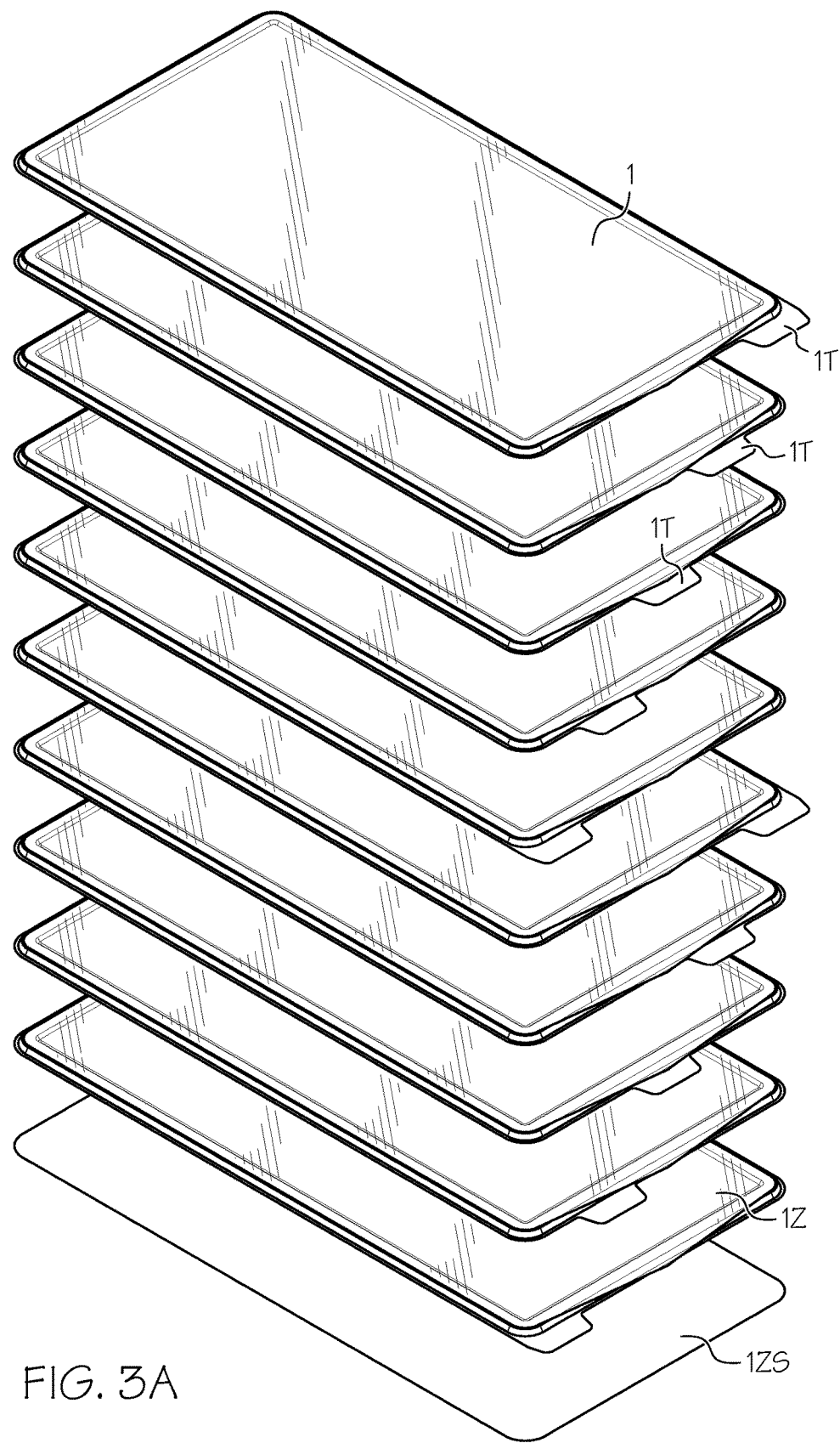
FIG. 3A is a perspective view of multiple sterile workspace layers of an embodiment of the present invention, with the layers spaced apart for illustration purposes only.
Figure 3B:
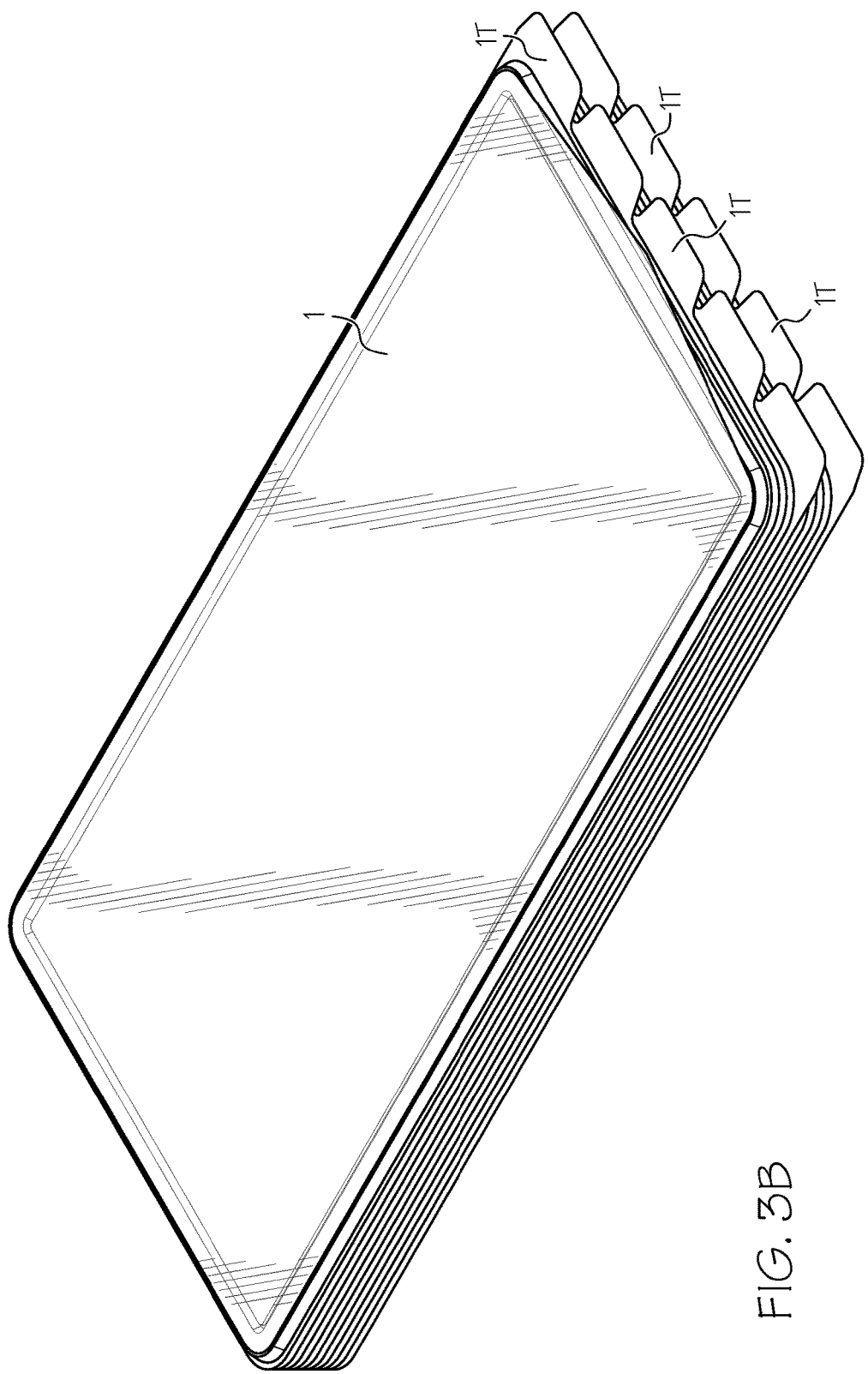
FIG. 3B is a perspective view of an embodiment of the assembly of the present invention.
Figure 3C:
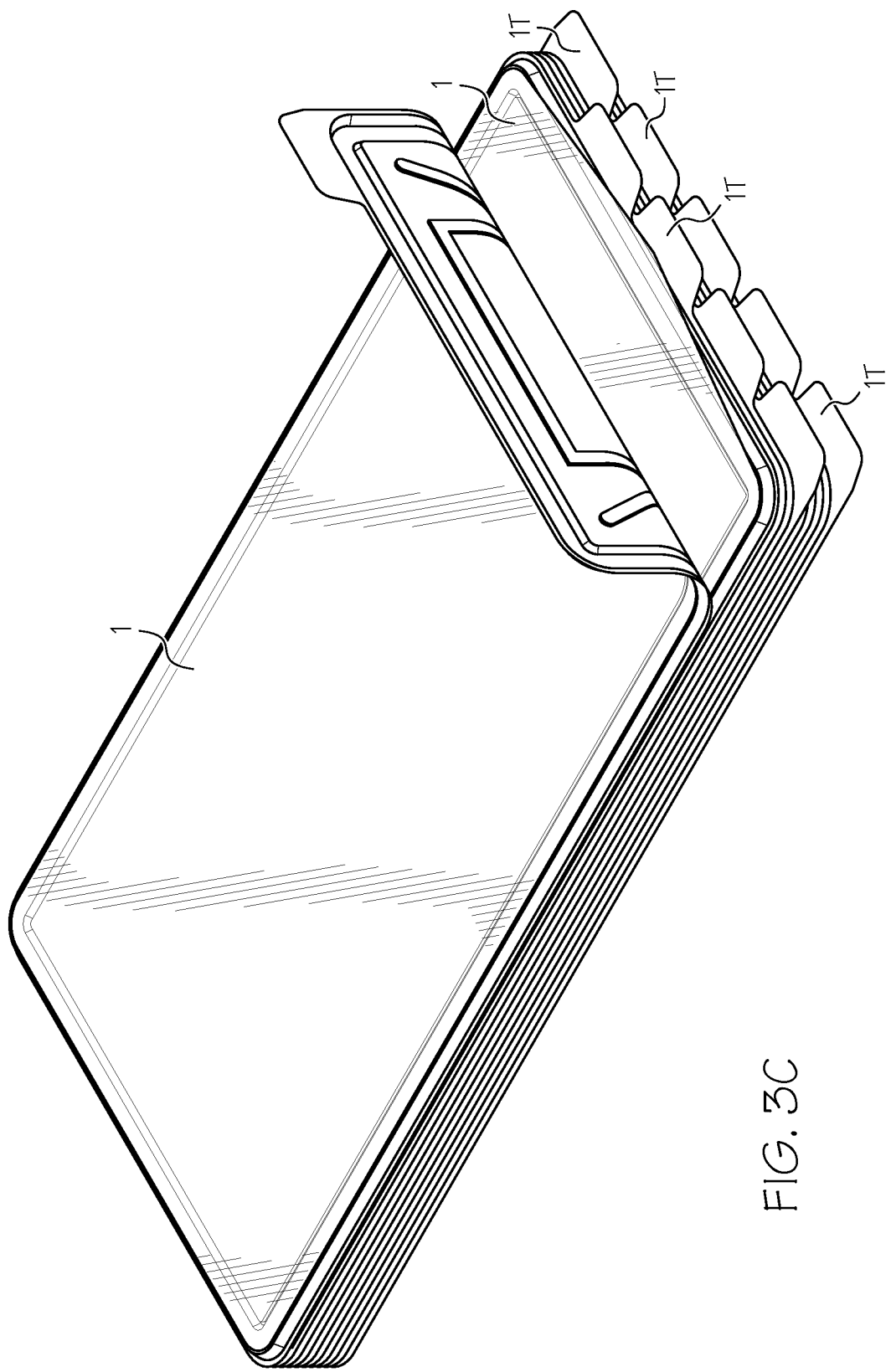
FIG. 3C is a perspective view of multiple sterile workspace layers of an embodiment of the present invention, with the first layer partially removed.

As shown in FIGS. 3A-3C, tabs (1T) may be affixed to or made a part of the trays of an assembly of the present invention, extending from and beyond a portion of the perimeter of the tray; in some embodiments the tabs (1T) extend about 0.75" beyond the perimeter of a tray. The tabs can provide a surface for data such as directions, patient data, and other information, including marketing information and logos. Spacing the tabs (1T) among trays in an assembly (as shown in FIGS. 3A-C) allows a user to remove the topmost tray by its tab without touching the tabs of subsequent workspace layers (depicted in FIG. 3C), minimizing the chance of cross contamination among tabs; in some embodiments the tabs may be spaced among successive trays by about 0.25" to 0.75", in some embodiments the tabs are spaced among successive trays by about 0.5".

Figure 4A:
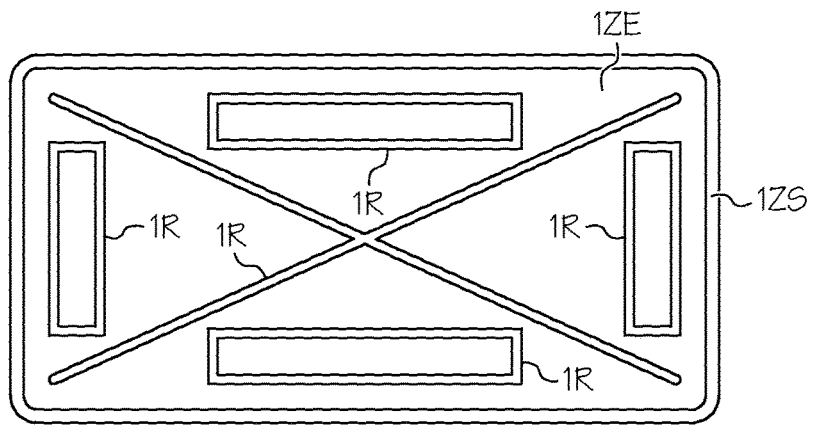
FIGS. 4A, 4B and 4C are, respectively, bottom views of different embodiments of the trays of an assembly of the present invention.
Figure 4B:
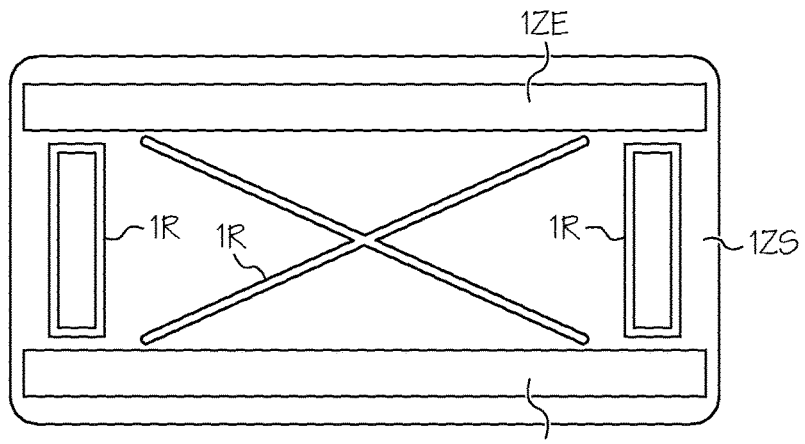
Figure 4C:
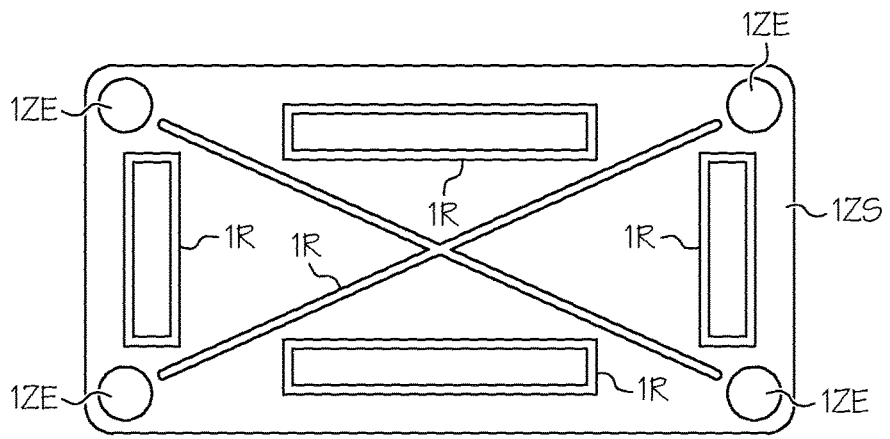

As shown in FIG. 3A and the embodiments shown in FIGS. 4A-4C, the bottom-most tray of each assembly may include a support surface (1ZS) with an adhesive or elastomer (1ZE) affixed thereto to prevent the tray from moving around unintentionally on the surface upon which it is placed. Alternatively, an adhesive or elastomer may be affixed to the bottom surface of the lowermost tray of the assembly of the present invention. As shown in FIGS. 4A-C, the elastomer (1ZE) may be a sheet or strips on the bottom of the support surface (1ZS) or the bottom tray (1), or any other configuration to facilitate adhesion or otherwise inhibit movement of the assembly to the work surface when in use. The elastomer may be a thermoplastic elastomer (TPE), such as Santoprene®, of sufficient hardness and high co-efficient of friction so as to prevent the tray from moving around the work surface when under the load of the complete assembly.

The workspace foam layer (2) of a workspace layer provides a sterile work surface when the system of the present invention is in use. As shown in FIGS. 1A, 1B and 2A-2C, the foam layer (2) is affixed to the top surface of the tray (1). The foam layer may be medical-grade, closed cell foam to create a non-absorbent, smooth surface; in some embodiments the closed cell foam is polyethylene. Alternatively the foam layer may be formed from polyurethane plastic. Other suitable materials for the foam layer include PVC film, ionomer resin, polyimide, polyester, polypropylene, or polycarbonate, or any combination thereof. In some embodiments the foam layer is coated with antibiotic preparations. Preferably the material selected for the foam layer minimizes the thickness thereof, while maintaining compression values suitable to cushion items placed on the surface during use. Suitable compression values include between about 3 psi and 40 psi, or between about 5 psi and 10 psi. In some embodiments the foam layer has a thickness of between about 0.01" and 0.1"; in some embodiments the foam layer has a thickness of about 0.04".

The dimensions of the workspace foam (2) may be sized in relationship to the size of the tray (1) to leave a channel (1C) between the perimeter of the foam (2) and the interior sides of the border (1A), as shown in FIGS. 1B and 2A-2C. By this configuration the channel (1C) collects incidental fluids flowing from the foam surface in use, which is particularly advantageous when the surface of the foam is non-absorbent. In an exemplary embodiment, where the tray (1) is sized 19.25"×10", with a raised border (1A) having a width of 0.375", the workspace foam (2) may be sized 18.05"×8.08".

The workspace foam layer (2) may be affixed to the tray (1) by means of an adhesive applied between the foam and the tray, wherein the adhesive has sufficient strength to retain the workspace foam on the tray during use. In some embodiments your inventors use a pressure sensitive adhesive (PSA) to secure the foam layer to the tray.

Figure 5A:
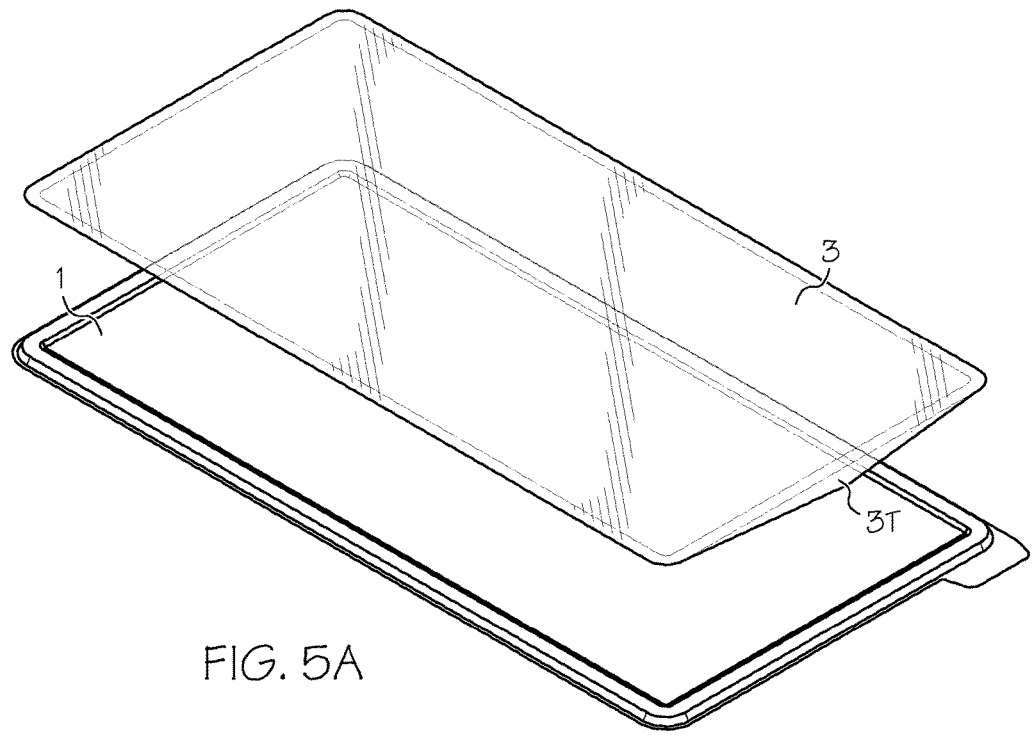
FIGS. 5A and 5B are perspective views of a layer of the assembly of the present invention, with a barrier layer shown separate from and affixed to the tray, respectively.
Figure 5B:
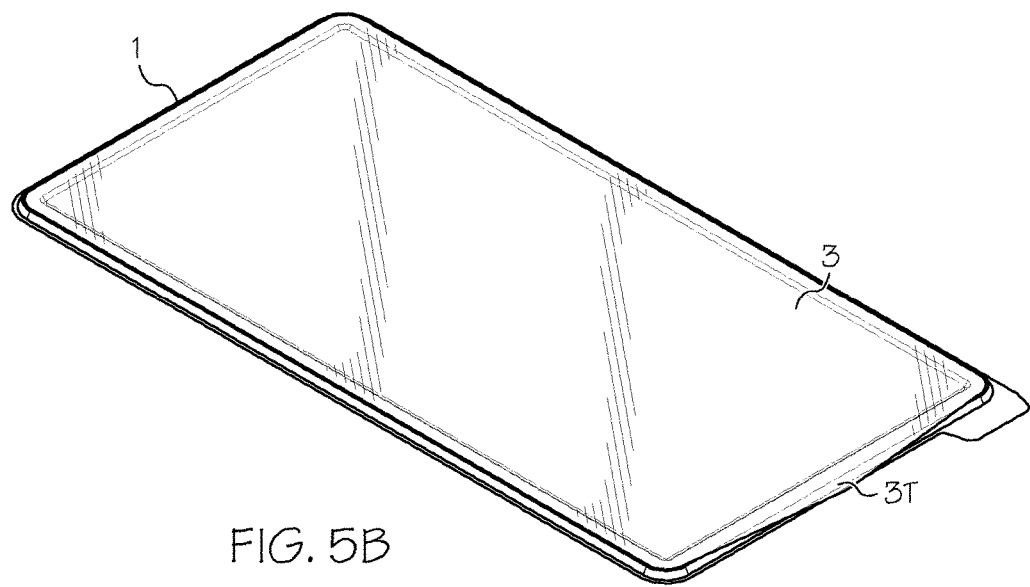

The barrier layer (3) of a workspace layer of an assembly of the present invention is a film intended to isolate the workspace layer of each tray, maintain sterility of the workspace and prevent contamination prior to use of the tray. The barrier film should be impervious to liquids, bacteria and viruses, providing an effective barrier to external contamination. As shown in FIGS. 2A-2C and 5A-5D, the barrier may be affixed to the tray (or its raised border) by heat sealing methods, or otherwise. The barrier layer may be a medical grade, low density polyethylene (LDPE). Alternatively, Tegaderm® film marketed by 3M is a suitable polyurethane plastic for use as the barrier layer (3) of the present invention, having a sterile top surface and a suitable amount of adhesive on the underside to removably fasten the layer to the tray. As shown in FIG. 1, in some embodiments one or more tabs (3T) are provided along one or more sides of the barrier layer (3) to assist in pealing the layer away from the tray when intended for immediate use. As shown in FIGS. 5A and 5B the barrier layer may be sized larger than the raised edge of the tray, in a polygonal shape so that it extends in a triangular shape at one end beyond the raised edge of the tray. In this configuration, a triangular shape forms the tab (3T) by which a user may grasp the film and pull back the same, exposing a sterile workspace, without the risk of contamination. Thereby, the sterility of the work surface is maintained until the barrier layer is removed.

By securing the barrier layer (3) to the raised border (1A) of the tray as shown in FIGS. 2A-2C and 5B-5D, the barrier layer may be provided with a certain degree of 'sag' or slack over the foam layer, as shown in FIGS. 2B-2C. Thereby, the film does not remain planar with the top of the border (1A) (as shown in FIG. 2A), and the sag may be absorbed in the depressed area of the tray (formed within the raised border) when a tray is placed above it in the layered assembly of the present invention, as shown in FIG. 2C. This sag allows trays to assemble more closely, decreasing the profile of the assembly of the present invention by 30-50%, and preventing lateral movement of the trays. Furthermore, the slack can be integral to maintaining the sterility of each workspace layer.

The barrier layer sag may be created by flexibility in the material of the barrier layer, or by having excess barrier layer material within the border of the tray when the barrier film is sealed to the edges of the tray. In some embodiments the sag allows the barrier layer to contact a portion of the workspace layer; in some embodiments the barrier layer contacts the entire workspace layer (2). The topmost layer of an assembly of the present invention may or may not provide sag or slack in the barrier layer.

In the layered assembly of the present invention, the bottom surface of each tray (1) may be secured to the barrier layer (3) of the tray immediately below it by means of a low-tack adhesive applied to the bottom surface of the tray. The peel force of the adhesive applied to the bottom surface of a tray (1) is sufficiently less than the peel force of the barrier layer (3) to its tray (1), so that the a workspace layer may be removed from the assembly, as shown in FIG. 3C, without removing the barrier layer in the subsequent workspace layer. Thereby, after use and contamination of a workspace layer, the layer may be removed by grasping the tab (1T) of the layer's tray (1) and pulling the tray off of the assembly, exposing another workspace layer with the barrier film intact on the tray, which workspace layer is maintained as sterile by this configuration until the barrier film is removed. The peel force of the adhesive applied to the bottom surface of the tray may be between about 0.1 psi and 5 psi, or 0.25 psi and 3.0 psi, or may be between about 0.5 psi and 1.5 psi, depending on the adhesive selected to secure the barrier layer to the tray. The peel force of the adhesive applied to the bottom surface of the tray may also be selected to allow the removal of the tray with one hand, without requiring a second hand to provide additional strength to hold down the remainder of the assembly when removing a tray. Meanwhile, the peel force of the adhesive used to secure the barrier layer to the tray may be between about 0.5 psi and 10.0 psi; in some embodiments the peel force is between about 0.75 psi and 5 psi; or may be between about 1.0 psi and 3.0 psi.

Figure 5C:
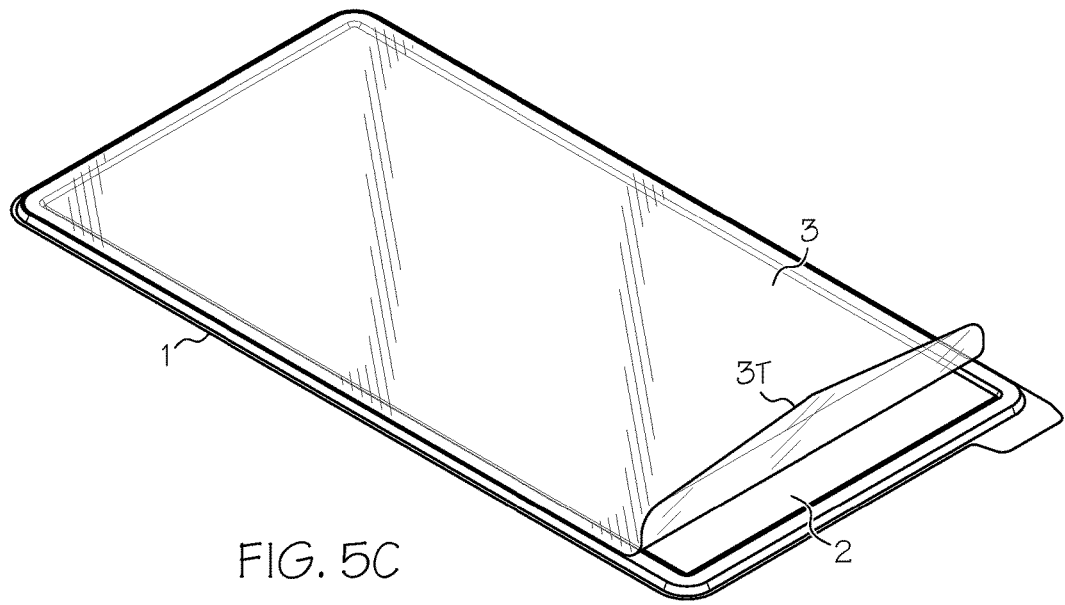
FIGS. 5C and 5D are perspective views of assemblies of the present invention, showing removal of the barrier layer.
Figure 5D:
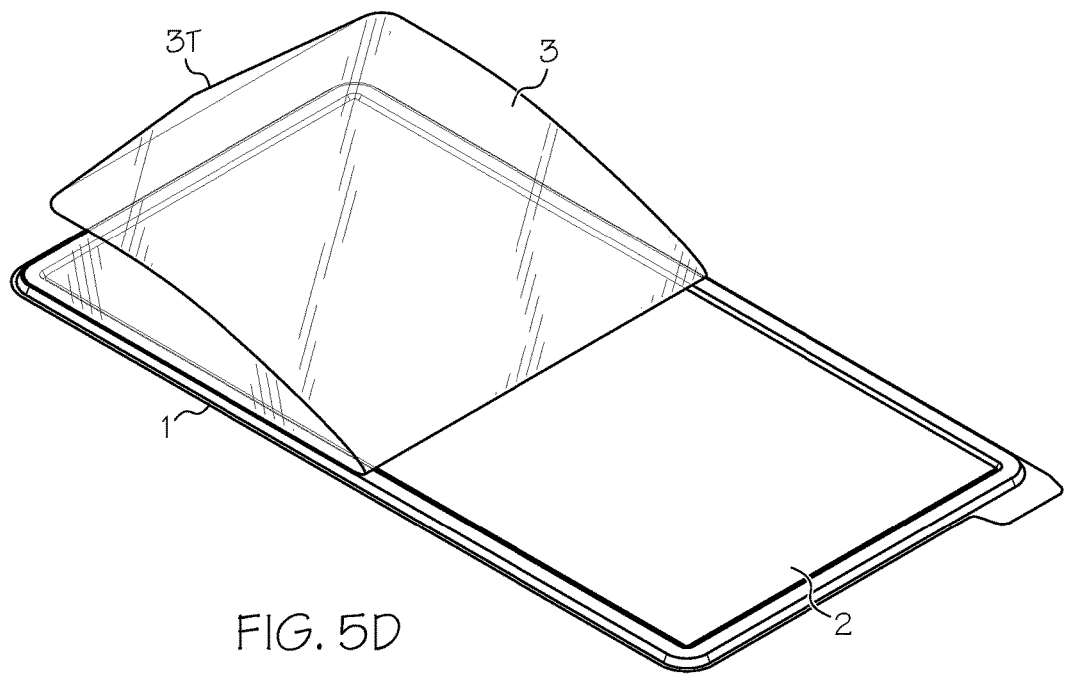

In practice, a sterilized assembly of this embodiment is provided, as shown in FIG. 3B; when the sterile workspace is required for a procedure, the barrier film (3) is removed from the upper-most tray, as shown in FIGS. 5C and 5D, by pulling on the tab (3T) of the film. A sterile workspace is now provided for use. This space may be discarded after use by removing the tray (1) of the top workspace layer, as shown in FIG. 3C, exposing a subsequent sterile layer with the barrier film intact until the sterile workspace is required. Critically, the sterility of the newly exposed workspace is maintained until the barrier layer thereof is removed.

Another configuration of the multi-layer adhesive assembly of the present invention includes a plurality of workspace layers (e.g., 10), as shown in FIG. 6. In this assembly each layer comprises a workspace foam (2) having a non-porous bottom surface, with a barrier layer (3) removably adhered to the top surface of the foam.

In some embodiments of this configuration, the workspace foam (2) as hereinabove described has a bottom surface of plastic to provide rigidity to the surface and the assembly, such as medical grade thermoplastic or HDPE, with an adhesive (e.g., PSA) bonding the foam to the plastic.

An adhesive strip (2B) may be placed on the bottom surface of the plastic to removably affix a first workspace layer to another workspace layer of the assembly. This adhesive (e.g., a PSA) has sufficient peel force so as to retain the workspace as part of the assembly until intentionally removed therefrom. The peel force of the adhesive applied to the bottom surface of the foam layer may be between about 0.5 psi and 15.0 psi, or about 1.0 psi and 7.0 psi, or may be between about 2.0 psi and 5.0 psi, depending on the adhesive selected to secure the barrier layer to the foam layer. In some embodiments this adhesive has a width between about 0.25" and 2.0", or between about 0.5" and 1.0", and a length about the same dimensions as the width of the foam layer, positioned at or near one side of the bottom surface of each layer.

The barrier layer film (3) removably affixed to each layer of workspace foam (2) is a medical grade film that seals the foam prior to use. The film may have a thickness of between about 0.001" and 0.01"; in some embodiments the film has a thickness of about 0.005". Affixed to or integrated with the bottom surface of the film is a layer of film adhesive with sufficient strength to retain the film on the workspace foam, while allowing the film to be removed from the workspace foam in preparation for use; however, the adhesive strength should be selected so that it does not overpower the adhesive selected for use between workspace layers, as hereinabove described; thereby, the barrier layer remains on the foam of its layer, while the foam of the layer above it is removed. The peel force of the adhesive used to secure the barrier layer to the foam layer may be between about 0.5 psi and 10.0 psi; in some embodiments the peel force is between about 0.75 psi and 5.0 psi; or may be between about 1.0 psi and 3.0 psi.

When the barrier layer (3) is removed from the workspace foam, the film adhesive releases from the workspace foam and remains intact on the film. In some embodiments the adhesive is applied around the perimeter of the film; in other embodiments it is applied to the undersurface of the film in contact with the foam layer. Further, in some embodiments the workspace is truncated at one or more of its corners (as shown in FIG. 6), and the portions of barrier film extending over the void left by the truncated portions of the workspace are free of adhesive to facilitate removal of the barrier film and minimize contact and time of contact when removing the film from the workspace foam, further reducing chances of cross contamination. In some embodiments the outermost perimeter of the film has no adhesive, which perimeter extends beyond the outside perimeter of the workspace foam, thereby acting as a shroud and preventing cross contamination among the layers in the assembly. In some embodiments tabs may be incorporated and extend from the perimeter of the barrier layer (3), spaced among layers to allow and facilitate the removal of the protective barrier.

Affixed to the bottom most workspace layer of some embodiments of the assembly in this configuration is a support surface (4), preferably an elastomeric sheet made from, for example, a thermoplastic, affixed to and having the same dimensions as the workspace foam. Other suitable materials for the foam layer include PVC film, ionomer resin, polyimides, polyester, polypropylene, or polycarbonate, or any combination thereof. This support surface may be between about 0.02" and 0.1"; in some embodiments this support surface is about 0.04" thick. The support surface has sufficient hardness to retain rigidity to the assembly when under the load of the complete stack and in use. Adhesive strips or other means of removably adhering the support surface (4) to a work surface are provided on the underside of the support surface to prevent the assembly from moving unintentionally on the work surface when in use, similar to that shown above in other configurations of the assembly of the present invention. Alternatively, the support surface (4) has a non-slip material (e.g., an elastomer) affixed or integrated with the underside of the support surface so that the assembly does not slide on the surface when in use.

In some embodiments of this configuration, and to further protect the sterility of the workspace layers, the assembly may be designed to have protective barrier layers (3) of decreasing dimensions (e.g., 0.1"-0.5", or about 0.2") from the top of the assembly to the bottom; likewise, the workspace foam (2) may have corresponding decreasing dimensions from the top workspace layer of the assembly to the bottom layer. In some embodiments of this configuration the barrier layers (3) may be crimped to cover the sides of the assembly.

In some embodiments of the assembly of the present invention the foam layer (2) is colored so that a user can identify where it is; in some embodiments the barrier layer (3) is colored so that a user can easily identify if the sterile sheet is exposed, or remains sterile under the barrier layer.

The number of workspace layers in an assembly of the present invention may be designed for the number of operations performed in a room in a day. For example, if ten operations are typically scheduled in a room, the assembly may include ten workspace layers. The height of the assembly varies based upon its components, and the individual height thereof, as well as the number of layers; in some embodiments of 8-12 layers, the assembly has a height of between about 0.85"-1.12".

The assemblies of the present invention and their components are sterilized using known sterilization methods, and delivered in packaging to preserve the sterilization of the assembly until removed for use; by means of the elements of the present invention sterilization can be maintained among unexposed (barrier layer in-tact) workspace layers.

The present invention is also suitable when sized and configured for use in various human and business environments, including for use on other surfaces in hospitals or medical facilities, baby changing tables, tables at restaurants, on airplane trays, and semi-conductor plant surfaces.

While the present invention has been described in reference to certain configurations and embodiments, it will be appreciated by those skilled in the art that the invention may be practiced otherwise than as specifically described herein without departing from the spirit and scope of the invention. It is, therefore, to be understood that the spirit and scope of the invention be only limited by the appended claims.

The invention claimed is:

1. A replaceable surface assembly to assist with the prevention of cross contamination comprising
   a plurality of layered sterile workspaces, each workspace comprising
      a tray having a planate surface and a bottom surface,
      a raised border about the perimeter of the tray and extending from the planate surface of the tray, to form a depressed area,
      a workspace foam layer affixed to the planate surface of the tray, and
      a barrier layer removably affixed to the raised border of the tray, the barrier layer being designed and configured to seal the depressed area of the workspace,
   wherein the bottom surface of a first workspace tray is removably secured to the barrier layer of a second workspace tray by a low-tack adhesive applied to the bottom surface of the first workspace tray, and
   wherein the barrier layer of the second workspace has a sag sufficient to allow the first workspace to nest into the depressed area of the second workspace.

2. The replaceable surface assembly of claim 1, wherein the tray is constructed of high-density polyethylene (HDPE).

3. The replaceable surface assembly of claim 1, wherein the raised border forms a recess sized to receive the raised border of a tray from another workspace.

4. The replaceable surface assembly of claim 1, wherein the tray further comprises one or more support structures to maintain the structural integrity of the tray.

5. The replaceable surface assembly of claim 1, further comprising a support surface with an elastomer affixed thereto.

6. The replaceable surface assembly of claim 1, wherein the workspace foam layer is sized in proportion to the dimensions of the tray to leave a channel between the foam's perimeter and interior sides of the tray formed by the raised borders.

7. The replaceable surface assembly of claim 1, wherein the barrier layer is removably affixed to the raised border of the tray by another adhesive applied near the circumference of the barrier layer, and wherein the another adhesive has a peel force greater than the adhesive applied to the bottom surface of the tray so that the first workspace tray may be removed from the assembly without removing the barrier layer of the second workspace.

8. The replaceable surface assembly of claim 1, wherein the tray further comprises a tab affixed to or made a part of the tray, extending from and beyond a portion of the tray's perimeter.

9. The replaceable surface assembly of claim 8, wherein the position of the tab on one workspace of the assembly is different than the position of the tab on another workspace of the assembly.

10. The replaceable surface assembly of claim 1, wherein the workspace foam layer comprises a closed cell foam.

11. The replaceable surface assembly of claim 10, wherein the closed cell foam is polyethylene.

12. The replaceable surface assembly of claim 1, wherein the barrier layer is a film removably affixed to the raised border of the tray.

13. The replaceable surface assembly of claim 12, wherein the barrier layer comprises low density polyethylene (LDPE).

\* \* \* \* \*